US012778414B2

(12) United States Patent
Preciado

(10) Patent No.: US 12,778,414 B2
(45) Date of Patent: Nov. 3, 2026

(54) NON-CONFOCAL POINT-SCAN FOURIER-DOMAIN OPTICAL COHERENCE TOMOGRAPHY IMAGING SYSTEM

(71) Applicant: Optos PLC, Dunfermline (GB)

(72) Inventor: Miguel Angel Preciado, Dunfermline (GB)

(73) Assignee: Optos plc, Dunfermline (GB)

( * ) Notice: Subject to any disclaimer, the term of this patent is extended or adjusted under 35 U.S.C. 154(b) by 439 days.

(21) Appl. No.: 18/197,059

(22) Filed: May 13, 2023

(65) Prior Publication Data

US 2023/0363639 A1 Nov. 16, 2023

(30) Foreign Application Priority Data

May 13, 2022 (EP) .................................... 22173231

(51) Int. Cl.
*A61B 3/10* (2006.01)
*A61B 3/00* (2006.01)
*A61B 5/00* (2006.01)

(52) U.S. Cl.
CPC ............ *A61B 3/102* (2013.01); *A61B 5/0066* (2013.01); *A61B 3/0025* (2013.01)

(58) Field of Classification Search
CPC ..... A61B 3/102; A61B 5/0066; A61B 3/0025; A61B 3/1015; A61B 3/107;
(Continued)

(56) References Cited

U.S. PATENT DOCUMENTS

2009/0021724 A1* 1/2009 Mahadevan-Jansen ..................... G01N 21/65 356/73
2010/0142041 A1* 6/2010 Berman .................. G02B 6/06 359/385
(Continued)

FOREIGN PATENT DOCUMENTS

JP 2012-115575 A 6/2012
JP 2016-194459 A 11/2016
WO 201453824 A1 4/2014

OTHER PUBLICATIONS

Hillmann, D., et al. "Aberration-Free Volumetric High-Speed Imaging of in Vivo Retina." Scientific Reports</i>, vol. 6, No. 1, Oct. 2016, p. 35209, doi:10.1038/SREP35209. (Year: 2016).*
(Continued)

*Primary Examiner* — Tarifur R Chowdhury
*Assistant Examiner* — Akbar H. Rizvi
(74) *Attorney, Agent, or Firm* — Faegre Drinker Biddle & Reath LLP

(57) ABSTRACT

A non-confocal point-scan Fourier-domain optical coherence tomography, OCT, imaging system, comprising: a scanning system arranged to perform a two-dimensional point scan of a light beam across an imaging target, and collect light scattered by the imaging target; a light detector arranged to generate a detection signal based on an interference between a reference light and the light collected by the scanning system. The OCT imaging system further comprises hardware arranged to: generate complex volumetric OCT data of the imaging target based on the detection signal, the OCT data including a component which, when the OCT data is processed to generate an enface projection of the OCT data, provides a defocusing and/or distortion in the enface projection; and generate corrected OCT data by executing a correction algorithm which uses phase informa-
(Continued)

tion in the OCT data to remove at least some of the component from the OCT data.

20 Claims, 6 Drawing Sheets

(58) Field of Classification Search
CPC ............ G01B 2290/65; G01B 9/02044; G01B 9/02077; G01B 9/02083; G01B 9/02091; G01B 9/02034; G01B 9/02043; G01B 9/02015; G01J 3/2823
See application file for complete search history.

(56) References Cited

U.S. PATENT DOCUMENTS

| | | | | |
|---|---|---|---|---|
| 2014/0226158 | A1* | 8/2014 | Trainer | G01J 3/453 356/336 |
| 2015/0216408 | A1* | 8/2015 | Brown | A61B 3/1015 351/215 |
| 2016/0000320 | A1* | 1/2016 | Sharma | G01J 3/2823 351/246 |
| 2017/0055831 | A1* | 3/2017 | Miwa | A61B 3/1225 |
| 2021/0038074 | A1 | 2/2021 | Koch | |
| 2022/0257111 | A1* | 8/2022 | Wang | A61B 3/102 |

OTHER PUBLICATIONS

"Computational optical coherence tomography" by Yuan-Zhi Liu, Fredrick A. South, Yang Xu, P. Scott Carney, and Stephen A. Boppart, Biomedical Optics Express, vol. 8, Issue 3, pp. 1549-1574 (2017).
"Digital focusing of OCT images based on scalar diffraction theory and information entropy" by Guozhong Liu, Zhongwei Zhi, and Ruikang K. Wang, Biomedical Optics Express, vol. 3, Issue 11, pp. 2774-2783 (2012).
"Computational high-resolution optical imaging of the living human retina" by Nathan D. Shemonski, Fredrick A. South, Yuan-Zhi Liu, Steven G. Adie, P. Scott Carney, and Stephen A. Boppart, Nature Photonics, vol. 9, pp. 440-443 (Jul. 2015).
"Full-field OCT: a non-invasive tool for diagnosis and tissue selection" by Claude Boccara, Fabrice Harms and Anne Latrive, SPIE (Jul. 12, 2013).
"In vivo Fourier-domain full-field OCT of the human retina with 1.5 million A-lines/s" by Tim Bonin, Gesa Franke, Martin Hagen-Eggert, Peter Koch, and Gereon Hüttmann, Optics Letters, vol. 35, Issue 20, pp. 3432-3434 (2010).
"Numerical focusing methods for full field OCT: a comparison based on a common signal model" by Abhishek Kumar, Wolfgang Drexler, and Rainer A. Leitgeb, Optics Express, vol. 22, Issue 13, pp. 16061-16078 (2014).
"Line-field confocal time-domain optical coherence tomography with dynamic focusing" by Arnaud Dubois, Olivier Levecq, Hicham Azimani, Arthur Davis, Jonas Ogien, David Siret, and Anaïs Barut, Optics Express, vol. 26, Issue 26, pp. 33534-33542 (2018).
"Line-field parallel swept source MHz OCT for structural and functional retinal imaging" by Daniel J. Fechtig, Branislav Grajciar, Tilman Schmoll, Cedric Blatter, Rene M. Werkmeister, Wolfgang Drexler, and Rainer A. Leitgeb, Biomedical Optics Express, vol. 6, Issue 3, pp. 716-735 (2015).
"Live video rate volumetric OCT imaging of the retina with multi-MHz A-scan rates" by Jan Philip Kolb, Wolfgang Draxinger, Julian Klee, Tom Pfeiffer, Matthias Eibl, Thomas Klein, Wolfgang Wieser, Robert Huber, PLOS One 14(3):e0213144 (2019).
"Computational adaptive optics for broadband optical interferometric tomography of biological tissue" by Steven G. Adiea, Benedikt W. Grafa, Adeel Ahmada, P. Scott Carneya, and Stephen A. Boppart, PNAS, May 8, 2012, vol. 109, No. 19, pp. 7175-7180.
Extended European Search Report (EESR) issued on Oct. 7, 2022 in relation to European patent application No. 22 173 231.6.13.
"Aberration-free volumetric high-speed imaging of in vivo retina" by D. Hillmann et al., Cornell University Library, Cornell University, Ithaca, NY 14853 May 12, 2016), XP 08701062.
"High-speed, digitally refocused retinal imaging with line-field parallel swept source OCT" by D. J. Fechtig et al., Progress in Biomedical Optics and Imaging, SPIE—International Society for Optical Engineering, vol. 9312 (Mar. 2, 2015), XP060046159.
"Simple approach for aberration-corrected OCT imaging of the human retina" by H. Sudkamp et al., Optics Letters, vol. 43, No. 17, p. 4224 (Aug. 27, 2018).

* cited by examiner

NON-CONFOCAL POINT-SCAN FOURIER-DOMAIN OPTICAL COHERENCE TOMOGRAPHY IMAGING SYSTEM

This application claims the benefit of priority of European Patent Application No. EP 22 173 231.6 filed May 13, 2022, the content of which is hereby incorporated by reference herein in its entirety, as if set forth fully herein.

FIELD

Example aspects herein generally relate to the field of Fourier-domain optical coherence tomography (OCT) systems and, in particular, to point-scan Fourier-domain OCT systems.

BACKGROUND

Optical coherence tomography (OCT) is an imaging technique based on low-coherence interferometry, which is widely used to acquire high-resolution two- and three-dimensional images of optical scattering media, such as biological tissue.

As is well-known, OCT imaging systems can be classified as being time-domain OCT (TD-OCT) or Fourier-domain OCT (FD-OCT) (also referred to as frequency-domain OCT), depending on how depth ranging is achieved. In TD-OCT, an optical path length of a reference arm of the imaging system's interferometer is varied in time during the acquisition of a reflectivity profile of the scattering medium being imaged by the OCT imaging system (referred to herein as the "imaging target"), the reflectivity profile being commonly referred to as a "depth scan" or "axial scan" ("A-scan"). In FD-OCT, a spectral interferogram resulting from an interference between the reference arm and the sample arm of the interferometer at each A-scan location is Fourier transformed to simultaneously acquire all points along the depth of the A-scan, without requiring any variation in the optical path length of the reference arm. FD-OCT can allow much faster imaging than scanning of the sample arm mirror in the interferometer, as all the back reflections from the sample are measured simultaneously. Two common types of FD-OCT are spectral-domain OCT (SD-OCT) and swept-source OCT (SS-OCT). In SD-OCT, a broadband light source delivers many wavelengths to the imaging target, and all wavelengths are measured simultaneously using a spectrometer as the detector. In SS-OCT (also referred to as time-encoded frequency-domain OCT), the light source is swept through a range of wavelengths, and the temporal output of the detector is converted to spectral interference.

OCT imaging systems can also be classified as being point-scan (also known as "point detection" or "scanning point"), line-scan or full-field, depending on how the imaging system is configured to acquire OCT data laterally. A point-scan OCT imaging system acquires OCT data by scanning a focused sample beam across the surface of the imaging target, typically along a single line (which may be straight, or alternatively curved so as to define a circle or a spiral, for example) or along a set of (usually substantially parallel) lines on the surface of the imaging target, and acquiring an axial depth profile (A-scan) for each of a plurality of points along the line(s), one single point at a time, to build up OCT data comprising a one- or two-dimensional array of A-scans representing a two-dimensional or three-dimensional (volumetric) reflectance profile of the sample.

Point-scan OCT systems are usually confocal, meaning that a confocal gate is present in the optical path before the interference light detector of the OCT system. This prevents light from points that are in the focal plane of the OCT scanner but not in the vicinity of its focal point from reaching the detector, thus improving the lateral resolution of the point-scan OCT system. Point-scan OCT systems typically employ a single-mode optical fibre to convey both the light going from an OCT light source to the imaging target and the return light coming from the imaging target to the interference light detector, with an end of the single-mode optical fibre core effectively providing both a point light source and a confocal gate.

However, in point-scan OCT imaging systems of this kind, which have optical components that give rise to significant optical aberration and/or defocusing (e.g. mirror-based OCT systems having ellipsoidal mirrors or the like, rather than lenses, in their scanning systems), the return light arriving at the plane of the confocal gate may have a significant proportion of its intensity distributed outside the confocal gate. This results in a reduced signal-to-noise ratio (SNR) in detection, which consequently lowers detection sensitivity and so reduces the imaging quality of the OCT imaging system. Similar problems can be caused by aberrations/defocusing originating in the imaging target, rather than the OCT imaging system itself. For example, in ophthalmic applications, where confocal point-scan OCT imaging systems are widely used to image the retina of an eye, scan location-dependent and patient-specific aberrations to the wavefront of the imaging light, caused by variations and possible imperfections in the curvatures of optical elements of the eye (primarily the cornea and lens), may limit the OCT imaging systems' sensitivity. In these applications, the aberrations tend to have greater effect when imaging the periphery of the retina and consequently also provide a limiting factor for the OCT imaging system's field-of-view over which acceptable image quality can be obtained. Efforts to address this problem have heretofore involved developing adaptive optics (AO) technology (including the hardware in wavefront sensor-based approaches to AO correction, and the algorithms used in wavefront sensor-less approaches) to allow it to more effectively compensate for, or correct, aberrations and the like.

SUMMARY

There is provided, in accordance with a first example aspect herein, a non-confocal point-scan Fourier-domain optical coherence tomography (FD-OCT) imaging system, comprising a scanning system arranged to perform a two-dimensional point scan of a light beam across an imaging target, and collect light scattered by the imaging target during the point scan, and a light detector arranged to generate a detection signal based on an interference light resulting from an interference between a reference light and the light collected by the scanning system during the point scan. The FD-OCT imaging system further comprises OCT data processing hardware arranged to: generate complex volumetric OCT data of the imaging target based on the detection signal, wherein the complex volumetric OCT data, when processed to generate an enface projection of the complex volumetric OCT data, provides an enface projection having at least one of a defocusing or a distortion therein; and generate corrected complex volumetric OCT data by executing a correction algorithm that uses phase information, which is encoded in the complex volumetric OCT data and may have a degree of phase stability, to correct the complex volumetric OCT data such that the corrected complex volumetric OCT data, when processed to generate an enface projection of the corrected complex volumetric OCT data, provides an enface projection having less of the at least one of the defocusing or the distortion than the enface projection of the complex volumetric OCT data.

There is provided, in accordance with a second example aspect herein, a computer-implemented method of processing complex volumetric OCT data of an imaging target generated by the non-confocal point-scan Fourier-domain OCT imaging system. The non-confocal point-scan Fourier-domain OCT imaging system comprises: a scanning system arranged to perform a two-dimensional point scan of a light beam across the imaging target, and collect light scattered by the imaging target during the point scan; a light detector arranged to generate a detection signal based on an interference light resulting from an interference between a reference light and the light collected by the scanning system during the point scan; and OCT data processing hardware arranged to generate the complex volumetric OCT data based on the detection signal, wherein the complex volumetric OCT data, when processed to generate an enface projection of the complex volumetric OCT data, provides an enface projection having at least one of a defocusing or a distortion therein. The method comprises acquiring the complex volumetric OCT data of the imaging target from the OCT data processing hardware, and generating corrected complex volumetric OCT data by executing a correction algorithm that uses phase information, which is encoded in the complex volumetric OCT data and may have a degree of phase stability, to correct the complex volumetric OCT data such that the corrected complex volumetric OCT data, when processed to generate an enface projection of the corrected complex volumetric OCT data, provides an enface projection having less of the at least one of the defocusing or the distortion than the enface projection of the complex volumetric OCT data.

In an example of the computer-implemented method set out above, the complex volumetric OCT data may comprise, as the phase information, a phase component whose a variation over at least a portion of the complex volumetric OCT data consists of a first component that is defined by a structure of the imaging target and a second component that is independent of the structure of the imaging target, and the corrected complex volumetric OCT data may be generated by executing a correction algorithm which uses the phase component to correct the complex volumetric OCT data, wherein the first component dominates over the second component in the variation of the phase component over the at least a portion of the complex volumetric OCT data such that the corrected complex volumetric OCT data, when processed to generate an enface projection of the corrected complex volumetric OCT data, provides an enface projection having less of the at least one of the defocusing or the distortion than the enface projection of the complex volumetric OCT data. Additionally or alternatively, respective items of phase information of the complex volumetric OCT data corresponding to each scan location on the imaging target 140 may have a phase stability during a respective interrogation time of the point (i.e. the duration of time over which light scattered from the scan location is collected by the scanning system 110 during the point scan) which allows the correction algorithm 132 to correct the complex volumetric OCT data such that the corrected complex volumetric OCT data, when processed to generate an enface projection of the corrected complex volumetric OCT data, provides an enface projection having less of the at least one of the defocusing or the distortion than the enface projection of the complex volumetric OCT data.

There is also provided, in accordance with a third example aspect herein, a computer program comprising computer-readable instructions which, when executed by a processor, cause the processor to perform the method of the second example aspect herein or the example thereof set out above. The computer program may be stored on a non-transitory computer-readable storage medium (such as a computer hard disk or a CD, for example) or carried by a computer-readable signal.

In the non-confocal point-scan FD-OCT imaging system set out above, the complex volumetric OCT data may comprise, as the phase information, a phase component whose variation over at least a portion of the complex volumetric OCT data consists of a first component that is defined by a structure of the imaging target, and a second component that is independent of the structure of the imaging target. The OCT data processing hardware may be arranged to generate the corrected complex volumetric OCT data by executing the correction algorithm which uses the phase component to correct the complex volumetric OCT data, wherein the first component dominates over the second component in the variation of the phase component over the at least a portion of the complex volumetric OCT data such that the corrected complex volumetric OCT data, when processed to generate the enface projection of the corrected complex volumetric OCT data, provides the enface projection having less of the at least one of the defocusing or the distortion than the enface projection of the complex volumetric OCT data. Additionally or alternatively, respective items of phase information of the complex volumetric OCT data corresponding to each scan location on the imaging target 140 may have a phase stability during a respective interrogation time of the point (i.e. the duration of time over which light scattered from the scan location is collected by the scanning system 110 during the point scan) which allows the correction algorithm 132 to correct the complex volumetric OCT data such that the corrected complex volumetric OCT data, when processed to generate an enface projection of the corrected complex volumetric OCT data, provides an enface projection having less of the at least one of the defocusing or the distortion than the enface projection of the complex volumetric OCT data.

The non-confocal point-scan Fourier-domain OCT imaging system may be an ophthalmic non-confocal point-scan Fourier-domain OCT imaging system, wherein the imaging target is an eye of a patient. In this case, the scanning system may be arranged to perform a two-dimensional point scan of a light beam across a portion of the eye, such that the eye is stationary with respect to the ophthalmic non-confocal point-scan Fourier-domain OCT imaging system on a time scale of the point scan, during which the scanning system performs the two-dimensional point scan of the light beam across the portion of the eye.

The non-confocal point-scan FD-OCT imaging system may further comprise a light beam generator comprising a light source, a light source aperture and a first optical system, the light source being arranged to emit light through the first optical system via the light source aperture to generate the light beam, wherein the light detector comprises a detection aperture and a second optical system, the light detector being arranged to detect the interference light propagating through the detection aperture via the second optical system, wherein a size of the detection aperture normalised to a focal length of the second optical system is larger than a size of the light source aperture normalised to a focal length of the first optical system. The light source aperture may be provided by an end of a core of a first optical fibre and the detection aperture may be provided by an end of a core of a second optical fibre. The first optical fibre may be a single-mode optical fibre, and the second optical fibre may be a multi-mode optical fibre.

In the non-confocal point-scan FD-OCT imaging system as set out above, the scanning system may comprise at least one scanning element and at least one curved mirror. The scanning system may be arranged to perform the two-dimensional point scan by the at least one scanning element scanning the light beam across the imaging target via the at least one curved mirror. The at least one curved mirror may comprise an ellipsoidal mirror.

The non-confocal point-scan FD-OCT imaging system may be a non-confocal point-scan spectral-domain OCT imaging system, or a non-confocal point-scan swept-source OCT imaging system, for example.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Figure 1:
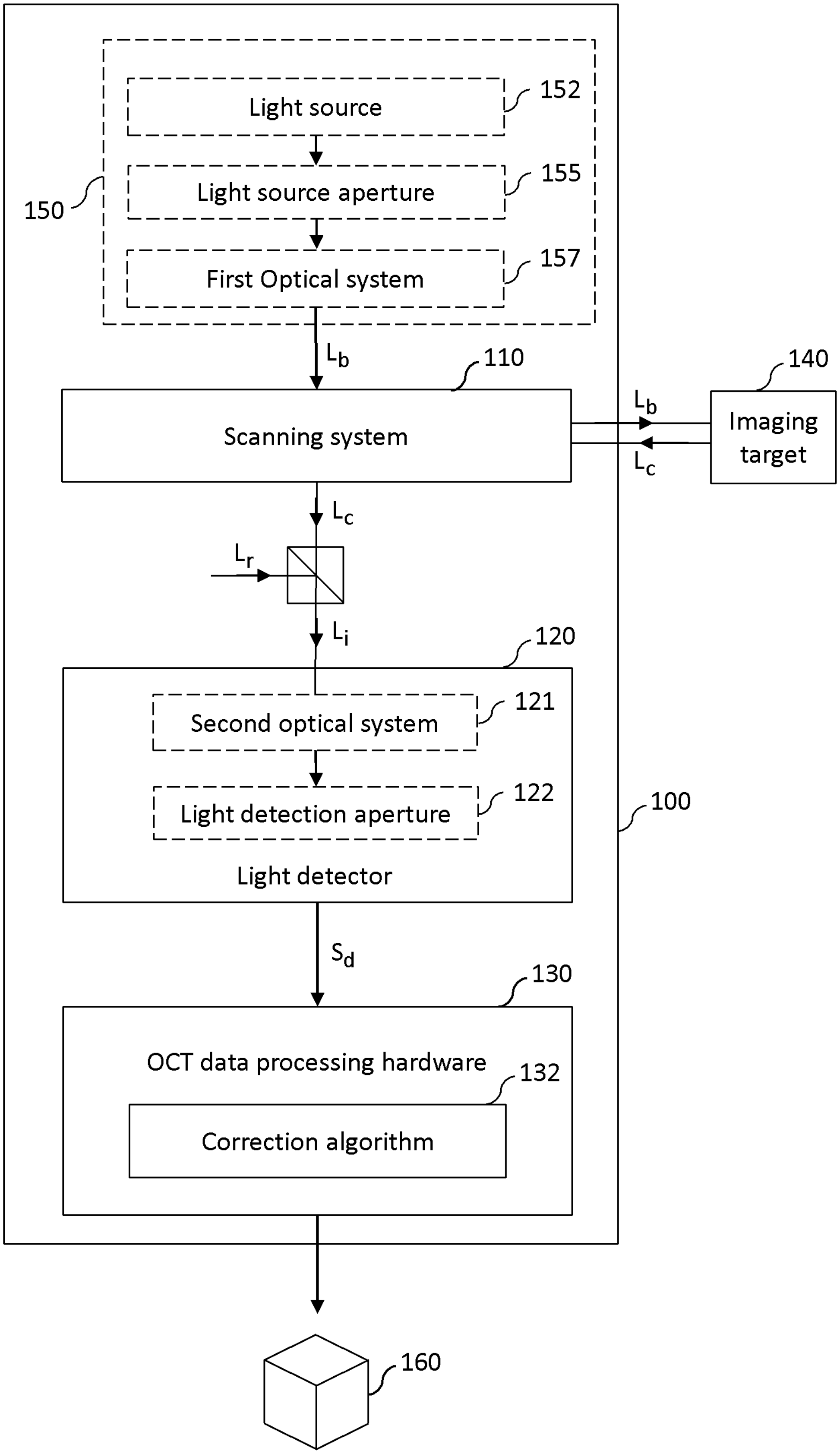
FIG. 1 is a schematic illustration of a non-confocal point-scan Fourier-domain OCT imaging system according to example embodiments herein.

In view of the shortcomings of conventional point-scan OCT imaging systems discussed above, the present inventor has recognised that detection sensitivity of Fourier-domain point-scan OCT imaging systems may be improved by departing from the established practice of making these systems confocal, which is typically achieved by the light scattered by the imaging target being collected through the same aperture as the light for illuminating the imaging target is originally launched, this aperture being an end of an optical fibre core in many common implementations. Moreover, the inventor has recognised that an improvement in detection sensitivity (or improved SNR) may be achieved by making the point-scan FD-OCT imaging system non-confocal, so that components of the return light from the imaging target, which would be blocked by the confocal gate in a confocal point-scan FD-OCT imaging system, are able to contribute to the interference light that is detected in the non-confocal point-scan FD-OCT imaging system. In an optical fibre-based implementation of the non-confocal point-scan FD-OCT imaging system, for example, non-confocality can be achieved by making the diameter of an optical fibre, whose end provides the detection aperture, larger than the diameter of another optical fibre, whose end provides the source aperture (via which the imaging target is illuminated). The deterioration in lateral resolution of an OCT imaging system having significant defocus and aberration, which would result from a loss of confocality in such a system, has heretofore made non-confocal point-scan FD-OCT imaging systems an unattractive proposition, and the problem of detection sensitivity has previously been addressed by adapting confocal OCT imaging systems to include adaptive optics hardware that compensates for aberrations in the imaging system's optics and/or the imaging target, for example as proposed in PCT application No. PCT/GB2013/052556 (published as WO 2014/053824 A1).

However, the inventor has also found that digital focusing techniques, which have been developed for refocusing images (e.g. enface projections or B-scans) from confocal point-scan FD-OCT imaging systems in order to remove the small degree of defocusing that typically occurs in these systems, can be applied to effectively mitigate the more extensive defocusing that may be observed in images from non-confocal point-scan FD-OCT imaging systems that are not well focused and/or have significant aberration, and therefore reduce or prevent the loss of lateral resolution that would otherwise arise in such systems. The inventor has found such digital focusing techniques to be applicable to non-confocal point-scan FD-OCT imaging systems despite certain complications that the loss of confocality introduces, which make this finding surprising. More particularly, in the case of a confocal point-scan FD-OCT imaging system, it can be demonstrated that taking an OCT measurement at a location on the imaging target is equivalent to a convolution with a phase term having a quadratic spatial variation at that location, which can be compensated for using numerical refocusing. In the case of a non-confocal point-scan FD-OCT imaging system, however, the applicability of such a phase term is prima facie unclear because the multiple interferences allowed by the lack of a confocal gate might be expected to add destructively. The inventor has found this not to be the case, and that known digital focusing techniques, which have previously been developed for refocusing images from confocal point-scan FD-OCT imaging systems, can be applied to effectively refocus images from non-confocal point-scan FD-OCT imaging systems.

First Example Embodiment

FIG. 1 is a schematic illustration of a non-confocal point-scan FD-OCT imaging system 100 according to example embodiments herein. The FD-OCT imaging system 100 comprises a scanning system 110, a light detector 120 and OCT data processing hardware 130. The non-confocal point-scan FD-OCT system 100 may, as in the first example embodiment, be a non-confocal point-scan swept-source OCT (SS-OCT) system 300, as shown in the more detailed illustration of the first example embodiment in FIG. 4. However, the non-confocal point-scan FD-OCT imaging system 100 need not be provided in this form and may, for example, take the alternative form of a spectral-domain OCT (SD-OCT) system 400, as in the case of the second example embodiment, which is described below with reference to FIG. 6. More generally, an example embodiment may be provided as any form of non-confocal point-scan FD-OCT imaging system that is capable of generating complex volumetric OCT data, i.e. Fourier transforms of respective spectral interferograms (interference spectra) representing complex A-scan information obtained for each scan location at which an OCT measurement is made during the two-dimensional point scan. Such complex volumetric OCT data encodes phase information from acquired OCT measurements that can be used by a correction algorithm as described herein to digitally refocus OCT image data.

The scanning system 110 is arranged to perform a two-dimensional point-scan of a light beam $L_b$ across an imaging target 140, and collect light $L_c$ which has been scattered by the imaging target 140 during the point scan. The scanning system 110 is therefore arranged to acquire A-scans at respective scan locations that are distributed two-dimensionally across a surface of the imaging target 140, by sequentially illuminating the scan locations with the light beam $L_b$, one scan location at a time, and collecting at least some of the light $L_c$ scattered by the imaging target 140 at each scan location. The scanning system 110 may perform the two-dimensional point-scan using any suitable scan pattern known to those versed in the art, for example a unidirectional scan (wherein a set of parallel scan lines are followed in a common direction, along which they extend), a serpentine scan or spiral scan.

In the present example embodiment, the FD-OCT imaging system 100 is an ophthalmic FD-OCT imaging system, which is arranged to acquire OCT data from an imaging target 140 in the form of a region of a retina of an eye, although any other part of the eye that can be imaged by OCT, such as a portion of the anterior segment of the eye, may alternatively or additionally form the imaging target 140. The scanning system 110 may be arranged to perform a two-dimensional point scan of the light beam $L_b$ across a portion of the eye, such that the eye is stationary with respect to the ophthalmic FD-OCT imaging system on a time scale of the point scan, during which the scanning system 110 performs the two-dimensional point scan of the light beam $L_b$ across the portion of the eye. The imaging target 140 is not, however, limited to a portion of an eye and may alternatively be any tissue (e.g. skin), biological sample or, more generally, any scattering medium whose sub-subsurface structure is to be imaged by OCT.

The FD-OCT imaging system 100 may further comprise a light beam generator 150 which includes a light source 152, a light source aperture 155, and a first optical system 157. In this case, the light source 152 is arranged to emit light through first optical system 157, via the light source aperture 155, to generate the light beam $L_b$, such that the shape and size (e.g. diameter, in case of the light source aperture 155 being circular) of the light source aperture 155 defines the cross-sectional shape and size (e.g. diameter) of the light beam $L_b$ (i.e. so that these sizes and shapes are the same). In some example embodiments, the light beam generator 150 may comprise further components (not shown in FIG. 1), such as one or more collimating lenses for collimating light from the light source 152, for example.

The light detector 120 is arranged to generate a detection signal $S_d$ based on an interference light $L_i$ resulting from an interference between a reference light $L_r$ and the light $L_c$ collected by the scanning system 110 during the point scan. In other words, the reference light and the light collected by the scanning system during the point scan are guided to coincide and interfere with one another, and the resulting interference light $L_i$ is directed to and received by light detecting components (not shown) of the light detector 120 via a second optical system 121 and a light detection aperture 122 of the light detector 120. The light detector 120 can thus detect the interference light $L_i$ propagating through the detection aperture 122 via the second optical system 121. The size (e.g. diameter) of the detection aperture 122 normalised to a focal length of the second optical system 121 is larger than the size (e.g. diameter) of the light source aperture 155 normalised to a focal length of the first optical system 157. In other words, a ratio of the size of the detection aperture 122 to the focal length of the second optical system 121 is larger than a ratio of the size of the light source aperture 155 to the focal length of the first optical system 157. The aperture size herein refers to a projection area on a plane perpendicular to the direction of light propagation through the aperture. The light detector 120 generates the detection signal $S_d$ by performing photoelectric conversion of the received interference light $L_i$. The specific form which the light detector 120 may take will depend on the form in which the non-confocal point-scan FD-OCT imaging system 100 is implemented. For example, where the FD-OCT imaging system 100 is implemented as an SD-OCT imaging system, the light detector 120 comprises a spectrometer, which may have a diffraction grating, Fourier transform lend, and a detector array (or a line scan camera). Where the FD-OCT imaging system 100 is implemented as a SS-OCT imaging system, as in the present example embodiment, the light detector 120 may comprise a balanced photodetector set-up comprising two photodetectors (e.g. reverse-biased photodiodes), whose output photocurrents are subtracted from one another, with the subtracted current signal being converted into a voltage detection signal by a transimpedance amplifier. The detection signal $S_d$ is then processed by the OCT data processing hardware 130.

The OCT data processing hardware 130 is arranged to generate complex volumetric OCT data of the imaging target 140, based on the detection signal $S_d$, using well-known data processing techniques. The complex volumetric OCT data, when processed to generate an enface projection of the complex volumetric OCT data (using any well-known projection technique, such as summed-voxel projection (SVP), or restricted SVP (RSVP), which restricts the SVP to a selected slab of the imaged sample), provides an enface projection having a defocusing (blurring) and/or a distortion in the enface projection image. In other words, the OCT data includes a component (e.g. phase errors, as discussed below) which, when the OCT data (or only a subset thereof) is processed to generate an enface projection of the OCT data (using any well-known projection technique, as noted above), provides a defocusing (blurring) and/or a distortion in the enface projection image. The defocusing and/or distortion in the enface projection (or other representation of the OCT data in image form, e.g. a B-scan image) may originate from aberrations in some of the optics within the FD-OCT imaging system 100, for example in one of more curved mirrors that may be provided in the scanning system 110. Alternatively or additionally, the defocusing and/or distortion may be caused by optical imperfections in the imaging target. Owing to the effect of the confocal gate in a conventional confocal point-scan FD-OCT imaging system, this defocusing and/or a distortion in the enface projection image is less significant in OCT data generated by such an imaging system, and may be suppressed using known numerical refocusing algorithms, for example as disclosed in the article titled "Digital focusing of OCT images based on scalar diffraction theory and information entropy" by G. Liu et al., Biomedical Optic Express, Vol. 3, Issue 11, pp. 2774-2783, the content of which is hereby incorporated by reference in its entirety.

The OCT data processing hardware 130 is further arranged to generate corrected complex volumetric OCT data 160 by executing a correction algorithm 132, which processes phase information that is encoded in the complex volumetric OCT data and has a degree of phase stability to correct the complex volumetric OCT data, such that the corrected complex volumetric OCT data 160, when processed to generate an enface projection of the corrected complex volumetric OCT data 160, provides an enface projection having less of the defocusing and/or distortion (i.e. a smaller degree (magnitude) of defocusing and/or distortion) than the enface projection of the complex volumetric OCT data. Put another way, the OCT data processing hardware 130 is further arranged to generate corrected complex volumetric OCT data 160 by executing a correction algorithm 132, which processes phase information encoded in the complex volumetric OCT data to remove or reduce at least some of the aforementioned component (i.e. the source of the defocusing and/or distortion present in the enface projection, which source lies in the complex volumetric OCT data) from the complex volumetric OCT data. In FD-OCT, complex data encoding the phase information can be obtained from a discrete Fourier transform (DFT) of the optical spectrum of the interference as measured by the FD-OCT imaging system.

The complex volumetric OCT data may comprise, as the phase information, a phase component whose variation over at least a portion of the complex volumetric OCT data comprises a first component that is defined by a structure of the imaging target 140, and a remaining second component that is independent of the structure of the imaging target 140. The OCT data processing hardware described 130, which is described in more detail below, may be arranged to generate the corrected complex volumetric OCT data by executing a correction algorithm 132 which uses the phase component to correct the complex volumetric OCT data, wherein the first component dominates over the second component in the variation of the phase component over the at least a portion of the complex volumetric OCT data such that the corrected complex volumetric OCT data 160, when processed to generate the enface projection of the corrected complex volumetric OCT data 160, provides the enface projection having less of the at least one of the defocusing or the distortion than the enface projection of the complex volumetric OCT data.

The OCT data processing hardware 130 thus takes the complex volumetric OCT data as an input to the correction algorithm 132, which is run to generate and output corrected complex volumetric OCT data 160, such that an enface projection of the corrected complex volumetric OCT data 160 has less of the defocusing and/or distortion than an enface projection of the input complex volumetric OCT data. The corrected complex volumetric OCT data 160 thus has at least some of the above-mentioned component (source) from the complex volumetric OCT data removed or reduced. As a result, enface projections of the corrected OCT data 160 show a decrease in defocusing and/or aberration-induced distortion, and so an improved lateral resolution relative to enface projections of the complex volumetric OCT data serving as input to the correction algorithm 132. The degree of (de) focusing in an enface projection image may be quantified using any one of a number of different ways known to those versed in the art. By way of example, the degree of defocusing may be quantified using a gradient-based, Laplacian-based, wavelet-based, statistics-based or discrete cosine transform-based focus measure operators. Various examples of such focus measure operators are provided in the article titled "Analysis of focus measure operators for shape-from-focus" by S. Pertuz et al., published in Pattern Recognition 46 (2013), pages 1415-1432, the content of which is hereby incorporated by reference in its entirety.

The correction algorithm 132 may be any numerical refocusing and/or aberration correction algorithm known in the art, which is capable of improving the lateral resolution in the enface projections of the corrected volumetric OCT data 160 by use of complex field information in the volumetric OCT data. Generally, the correction algorithm 132 applies a phase filter to the complex volumetric OCT data in the Fourier domain, before taking the inverse Fourier transform of the result. The phase filter is selected to reduce or remove phase errors which would produce the defocusing/distortion in an enface projection of the complex volumetric OCT data. An appropriate phase filter can be derived from a mathematical model of the FD-OCT imaging system.

By way of an example, the correction algorithm 132 may take the form of the fully automated aberration correction algorithm as described in the article titled "Computational high-resolution optical imaging of the living human retina" by N. D. Shemonski et al., Nature Photonics Vol. 9 (2015): pp. 440-443, the content of which is hereby incorporated by reference in its entirety (including the supplementary sections therein). In the described aberration correction algorithm, a Fourier transform of the complex volumetric OCT data is multiplied by a phase filter, before an inverse Fourier transform is applied. This phase filter computationally mimics the function of a Shack-Hartmann wavefront sensor, although it may also be adapted to include a defocusing correction, as explained in the aforementioned article by N. D. Shemonski et al. A peak detection metric may be applied in conjunction with a guide-star based algorithm to iteratively fine-tune the aberration correction.

As another example, the correction algorithm 132 may take the form of the digital refocusing method in "Digital focusing of OCT images based on scalar diffraction theory and information entropy" by G. Liu et al., Biomed. Opt. Express 3, pp. 2774-2783 (2012), the content of which is hereby incorporated by reference in its entirety. The described digital refocusing method comprises taking the Fourier transform of the complex volumetric OCT data and rescaling it into linear k-space. This data is then resampled in the axial direction to obtain a sequence of enface frames along the axial direction. These enface frames are then digitally refocused onto a new focal plane by performing a search for a focal distance that minimises an entropy function of the image as it varies with each distance (such as a distance corresponding to the image with the minimum Shannon entropy out of a range of refocused images at differing focal distances). Once all enface frames have been refocused along the axial direction, the refocused enface frames have an inverse Fourier transform applied to them such that refocused image domain volumetric OCT data is obtained.

It should be noted, however, that the correction algorithm 132 is not limited to the examples set out above. The correction algorithm 132 may, for example, take the alternative form of one of the computational aberration correction algorithms, digital refocusing algorithms and interferometric synthetic aperture microscopy algorithms disclosed and/or referenced in "Computational optical coherence tomography [Invited]" by Y. Liu et al., Biomed. Opt. Express 8, pp. 1549-1574 (2017), the content of which is hereby incorporated by reference in its entirety.

As noted in Section 6 of the aforementioned article by Y. Liu et al., the respective phase information of the complex volumetric OCT data corresponding to each point in the imaging target 140 is required to have a phase stability during the respective interrogation time of the point (i.e. the duration of time over which light scattered by the point is collected by the scanning system 110 during the point scan) which allows the correction algorithm 132 to correct the complex volumetric OCT data. The requisite phase stability depends on the implementation of correction algorithm 132 and may be achieved either by appropriate configuration of the hardware of the non-confocal point-scan FD-OCT imaging system 100 or by post-processing of the complex volumetric OCT imaging data (which may be a part of the correction algorithm 132), as set out below. Further increasing the phase stability of the non-confocal point-scan FD-OCT imaging system 100 may improve the effectiveness of the correction algorithm 132 in reducing the defocusing and/or distortion present in the enface projection of the corrected complex volumetric OCT data 160.

In other words, in the non-confocal point-scan FD-OCT imaging system 100 set out above, the complex volumetric OCT data may comprise a phase component whose variation over at least a portion of the complex volumetric OCT data comprises a first component that is defined by a structure of the imaging target 140 and, in particular, the way the structure scatters the incident light beam as the beam is scanned through the structure. The remaining variation of the phase component is independent of the structure of the imaging target 140 (such that the phase component consists of the first component and a remaining second component that is independent of the structure of the imaging target 140). The OCT data processing hardware 130 may be arranged to generate the corrected complex volumetric OCT data 160 by executing the correction algorithm 132, which uses the phase component to correct the complex volumetric OCT data, wherein the first component dominates the variation of the phase component over the at least a portion of the complex volumetric OCT data (i.e., the first component dominates over the second component in the variation of the phase component over the at least a portion of the complex volumetric OCT data) such that the corrected complex volumetric OCT data 160, when processed to generate the enface projection of the corrected complex volumetric OCT data 160, provides the enface projection having less of the at least one of the defocusing or the distortion than the enface projection of the complex volumetric OCT data.

Such improvements in the phase stability of a point-scan FD-OCT imaging system may be achieved via appropriate configuration of imaging hardware and/or post-processing methods, as described in the article by Y. Liu et al., for example. For example, the non-confocal point-scan OCT imaging system 100 may be configured to image at high enough speeds to achieve at least partial phase stability, for example such that the duration of the two-dimensional point scan is substantially less (e.g. by an order of magnitude or more) than an average (or, preferably, smallest) time period of motion artifacts within the non-confocal point-scan FD-OCT imaging system 100, such as those induced by patient movement or by jitter in one or more of elements in scanning system 100. For example, where the non-confocal point-scan FD-OCT imaging system 100 is an ophthalmic FD-OCT imaging system, wherein the imaging target 140 is an eye of a patient and the scanning system 110 is arranged to perform a two-dimensional point scan of a light beam across a portion of the eye, the eye may be stationary with respect to the ophthalmic FD-OCT imaging system on a time scale on which the scanning system 110 performs the two-dimensional point scan. This may be achieved by the scanning system 110 being arranged to perform the two-dimensional point scan at a scanning speed greater than or equal to 100 kHz, for example. The scanning speed may be characterized by the axial depth scan rate (A-scan rate or line rate). For SS-OCT systems, the scanning speed may be given by the sweep repetition rate, and for SD-OCT by the line rate of the applied line scan camera.

Other demonstrated hardware methods include the coupling of the OCT imaging system to its imaging target, the introduction of a fixed phase reference object near the sample, and within the OCT image, to provide a reference point for axial motion corrections and the use of an additional speckle-tracking imaging sub-system to correct for transverse motion, as described further in the article by Y. Liu et al.

One possible post-processing method (which may form a part of the correction algorithm 132) uses the complex conjugate multiplication of adjacent fast-axis frames (i.e., the B-scans in a parallel two-dimensional point scan) to determine the phase difference between the frames and thus correct for axial motion along the slow axis of an OCT imaging system, as described further in the article by Y. Liu et al. The use of post-processing methods can reduce the imaging speed requirements on an OCT imaging system that are necessary to attain a similar phase stability.

The stability considerations set out above are further elaborated on in "Stability in computed optical interferometric tomography (Part I): Stability requirements" by N. Shemonski et al., Opt. Express 22, pp. 19183-19197 (2014), the content of which is hereby incorporated by reference in its entirety.

Figure 2:
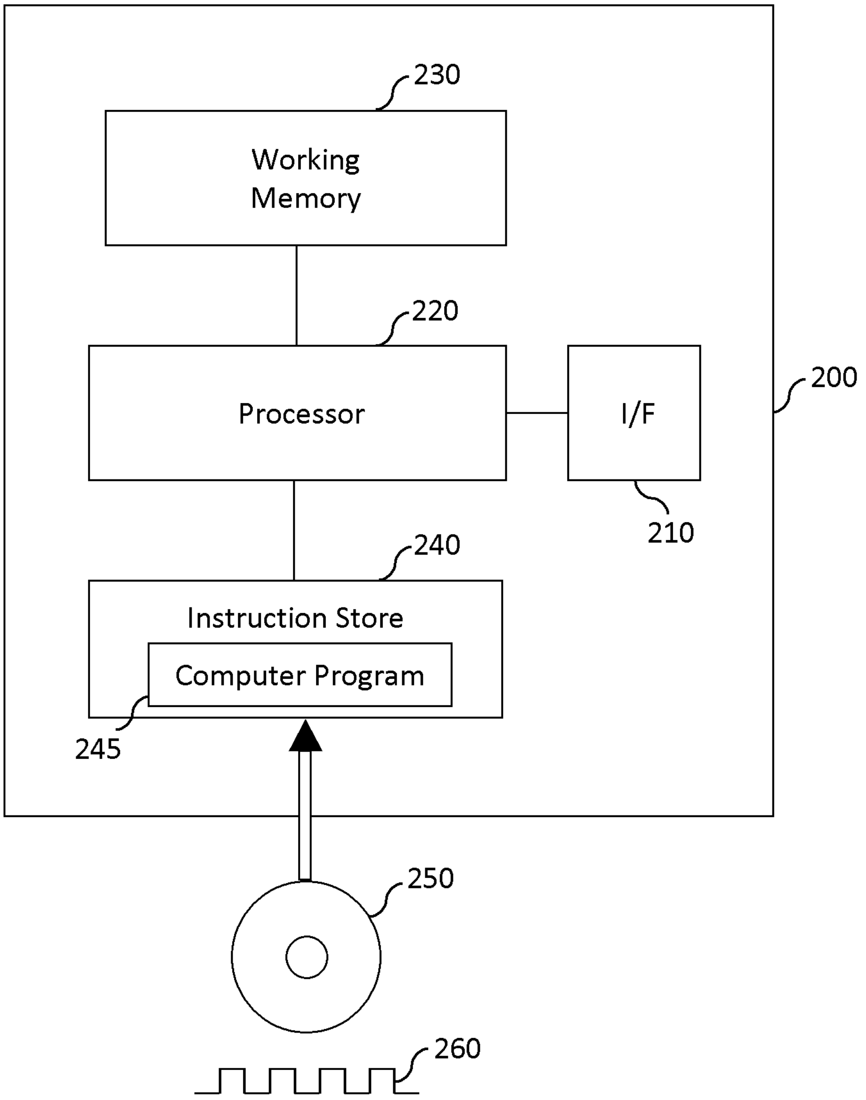
FIG. 2 is a schematic illustration of a programmable signal processing hardware, which may be configured to perform the functions of the OCT data processing hardware described herein.

The OCT data processing hardware 130 may be provided in any suitable form, for example as a programmable signal processing hardware 200 of the kind illustrated schematically in FIG. 2. The programmable signal processing apparatus 200 comprises a communication interface (I/F) 210, for receiving the detection signal $S_d$ from the light detector 120, and outputting the corrected complex volumetric OCT data 160 and/or a graphical representation thereof (for example, in the form of an enface projection of the corrected complex volumetric OCT data 160) for displaying on a display, such a computer screen or the like. The signal processing hardware 200 further comprises a processor (e.g. a Central Processing Unit, CPU, and/or a Graphics Processing Unit, GPU) 220, a working memory 230 (e.g. a random-access memory) and an instruction store 240 storing a computer program 245 comprising the computer-readable instructions which, when executed by the processor 220, cause the processor 220 to perform various functions including those of the OCT data processing hardware 130 described herein. The working memory 230 stores information used by the processor 220 during execution of the computer program 245. The instruction store 240 may comprise a ROM (e.g. in the form of an electrically erasable programmable read-only memory (EEPROM) or flash memory) which is pre-loaded with the computer-readable instructions. Alternatively, the instruction store 240 may comprise a RAM or similar type of memory, and the computer-readable instructions of the computer program 245 can be input thereto from a computer program product, such as a non-transitory, computer-readable storage medium 250 in the form of a CD-ROM, DVDROM, etc. or a computer-readable signal 260 carrying the computer-readable instructions. In any case, the computer program 245, when executed by the processor 220, causes the processor

220 to perform the functions of the OCT data processing hardware 130 as described herein. In other words, the OCT data processing hardware 130 of the example embodiment may comprise a computer processor 220 and a memory 240 storing computer-readable instructions which, when executed by the computer processor 220, cause the computer processor 220 to generate complex volumetric OCT data of the imaging target based on the detection signal $S_d$ from the light detector 120, wherein the complex volumetric OCT data, when processed to generate an enface projection of the complex volumetric OCT data, provides an enface projection having at least one of a defocusing or a distortion in the enface projection. Further, the computer-readable instructions, when executed by the computer processor 220, cause the computer processor 220 to execute the correction algorithm 132 to remove at least some of the component from the OCT data to produce corrected OCT data 160, as described herein.

It should be noted, however, that the OCT data processing hardware 130 may alternatively be implemented in non-programmable hardware, such as an ASIC, an FPGA or other integrated circuit dedicated to performing the functions of the OCT data processing hardware 130 described above, or a combination of such non-programmable hardware and programmable hardware as described above with reference to FIG. 2.

Figure 3:
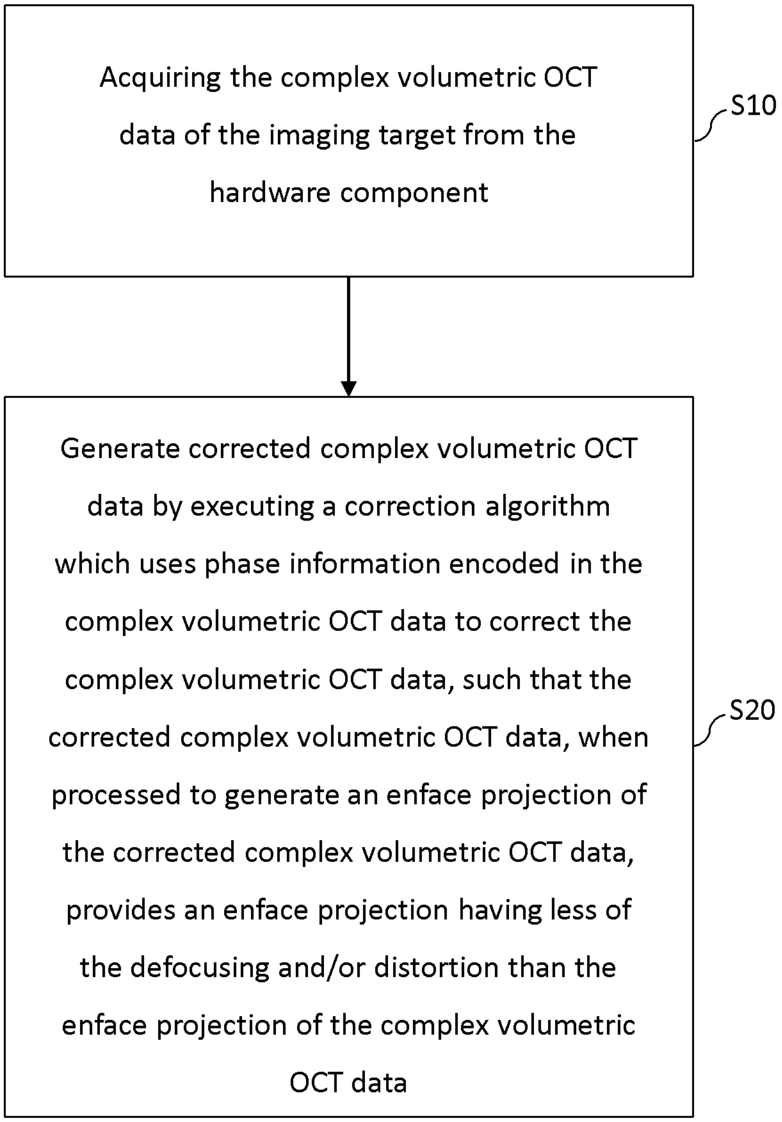
FIG. 3 is a flow diagram illustrating a process of generating corrected complex volumetric OCT data according to an example embodiment.

FIG. 3 is a flow diagram illustrating a process (complex volumetric OCT data correction algorithm) by which the OCT data processing hardware 130 of the example embodiment generates the corrected complex volumetric OCT data 160 by executing the correction algorithm 132, which processes phase information encoded in the complex volumetric OCT data to correct the complex volumetric OCT data.

In process S10 of FIG. 3, the OCT data processing hardware 130 acquires the complex volumetric OCT data of the imaging target 140 that has been previously generated thereby, for example by retrieving this data from a memory (e.g. working memory 230 shown in FIG. 2) of the OCT data processing hardware 130.

Then, in process S20 of FIG. 3, the OCT data processing hardware 130 generates the corrected complex volumetric OCT data 160 by executing the correction algorithm 132 described above, thus removing at least some of the component from the complex volumetric OCT data.

The process of FIG. 3 may be performed by OCT data processing hardware 130 implemented in the form of a programmable signal processing hardware 200 as described above with reference to FIG. 2, which operates in accordance with instructions included in a complex volumetric OCT data correction computer program when the computer program is executed by one or more processors. This computer program may be stored in a computer program product, such as a non-transitory, computer-readable storage medium in the form of a CD-ROM, DVDROM, etc. or a computer-readable signal carrying the computer-readable instructions.

The complex volumetric OCT data correction computer program may form part of a computer program which also generates the complex volumetric OCT data of the imaging target 140 based on the detection signal $S_d$, or it may alternatively be a separate program, which may or may not be executed by the same one or more processors that generate the complex volumetric OCT data of the imaging target 140 based on the detection signal $S_d$. In implementations where the complex volumetric OCT data correction computer program is executed by a first set of one or more processors, while the complex volumetric OCT data of the imaging target 140 is generated on the basis of the detection signal $S_d$ by a second set of (different) one or more processors, the first set of one or more processors may acquire the complex volumetric OCT data of the imaging target 140 in process S10 of FIG. 3 by receiving this data from the second set of one or more processors via appropriate interfaces between the two sets of processors.

Figure 4:
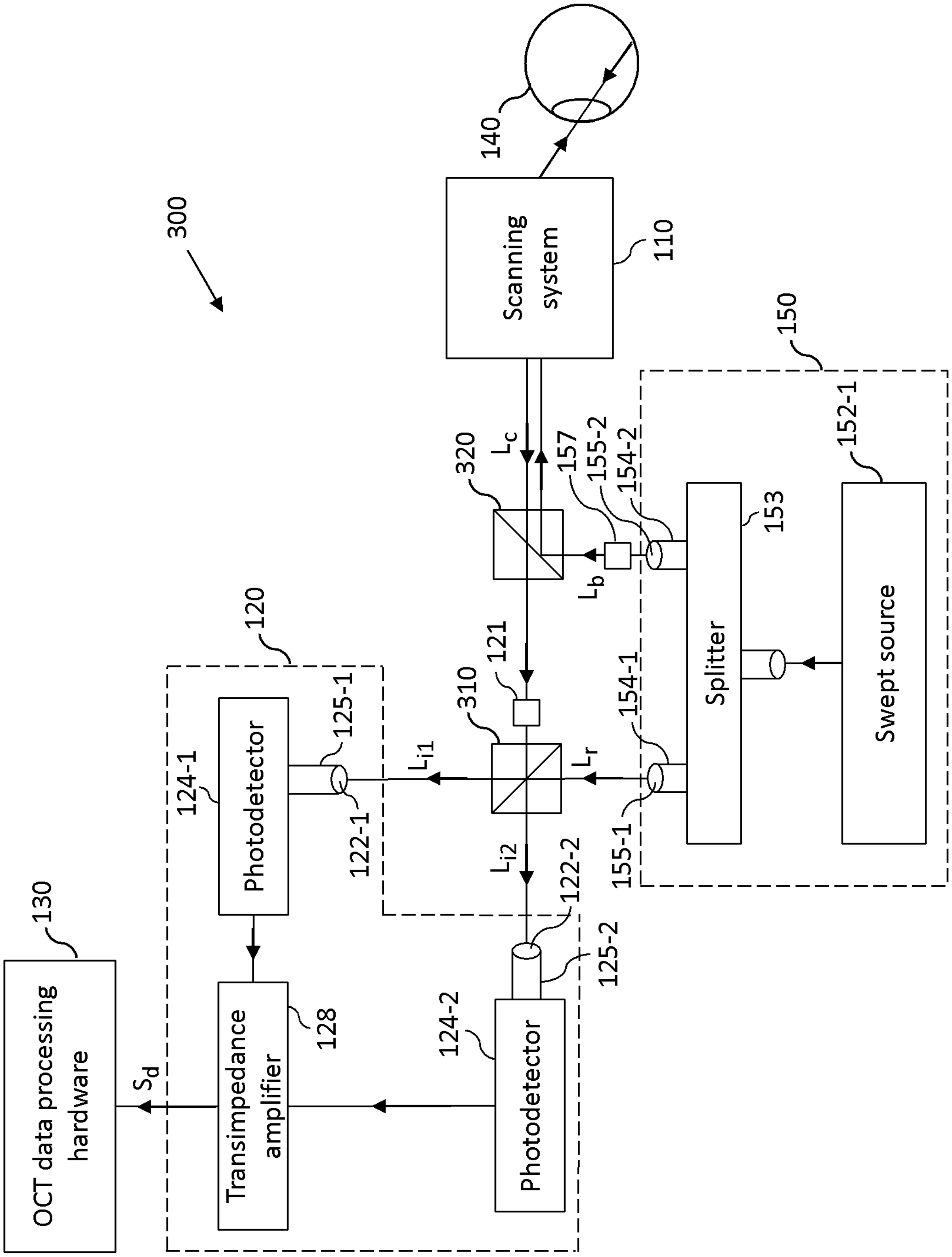
FIG. 4 is a schematic illustration of a non-confocal point-scan swept-source OCT imaging system according to a first example embodiment herein.

FIG. 4 shows further details of the non-confocal point-scan FD-OCT system of the first example embodiment herein and, in particular, how its component parts may be implemented in case the FD-OCT imaging system 100 is provided in the form of a non-confocal point-scan swept-source OCT (SS-OCT) imaging system 300.

As shown in FIG. 4, the light beam generator 150 comprises a swept light source 152-1 in the form of a wavelength-swept (or "tuneable") laser, for example, which is arranged to vary the wavelength of the laser light output thereby across a range of wavelengths over time (preferably linearly), whilst maintaining a narrow instantaneous linewidth. The tuneable laser may be of type known to those versed in the art, such as one based on a Fourier-domain mode-locking (FDML) laser with a Fabry-Perot tuneable filter or polygonal scanning mirror, or a microcavity tuneable laser with microelectromechanical systems (MEMS), for example. The median frequency of the swept source 152-1 is selected in dependence on the imaging target, and is usually in the near-infrared or infrared part of the spectrum (typically about 1050 nm) in ophthalmic applications, for example.

The light output by the swept source 152-1 is coupled into an optical fibre and then split into two parts by splitter 153, which may, as in the fibre-optic implementation of the present example embodiment, be a fibre-optic coupler. The splitter 153 may alternatively be provided in the form of a beam splitter in an alternative, free-space implementation of the SS-OCT imaging system 300. One of the outputs of the splitter 153 follows a first optical path to beam splitter 310 via a first optical fibre 154-1. A second output of the splitter 153 follows a second optical path to a beam splitter 320 via a second optical fibre 154-2. The first optical fibre 154-2 is thus arranged to guide light from the swept source 152-1 to the scanning system 110 (via the optional beam splitter 320). The optical fibres 154-1 and 154-2 are preferably single-mode optical fibres.

The end of the core of the first optical fibre 154-1, from which a reference light beam $L_r$ is incident on beam splitter 310, provides a reference light aperture 155-1, and the end of the core of the second optical fibre 154-2, from which a light beam $L_b$ is incident on beam splitter 320, provides a light source aperture 155-2. However, in an alternative, free-space implementation of the SS-OCT imaging system 300, where the splitter 153 is a beam splitter, the size of light beam $L_b$ and the reference light beam $L_r$ may be set by the swept light source 152-1 via a pinhole, window or the like that is a part of the swept light source 152-1.

The beam splitter 320 reflects light beam $L_b$ to the scanning system 110, which is arranged to perform a two-dimensional point-scan of the light beam $L_b$ across the imaging target 140, and collect light scattered by the imaging target 140 during the point-scan.

Figure 5:
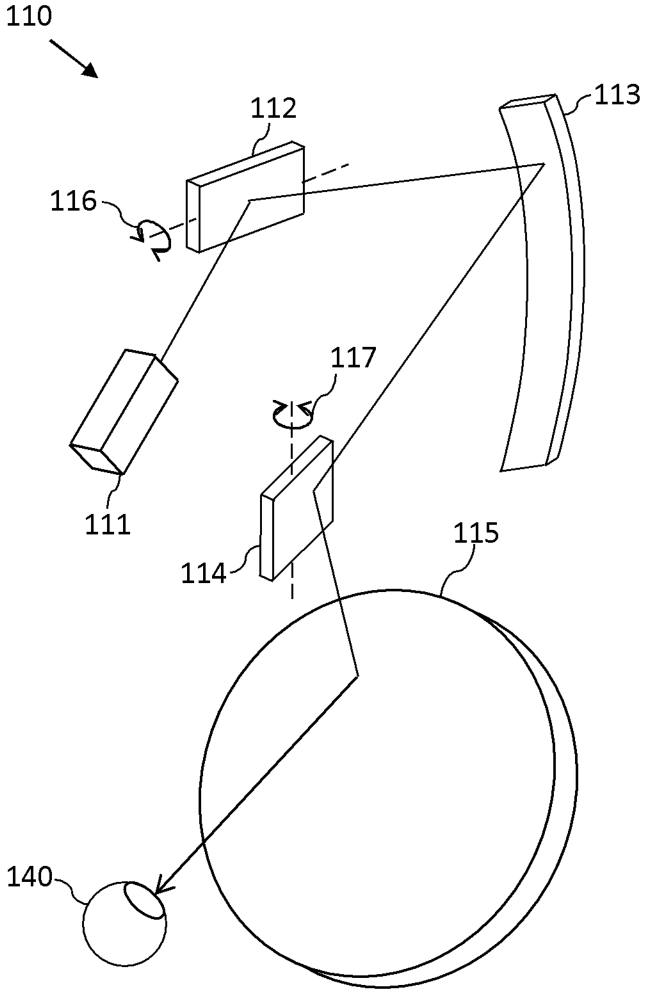
FIG. 5 is a schematic illustration of an example scanning system which is included in the example embodiments.

The scanning system 110 may, as in the present example embodiment, comprise a scanning element and a mirror, wherein the scanning system 110 is arranged to perform the two-dimensional point scan by the scanning element scanning the light beam $L_b$ across the imaging target 140 via the mirror. An example of such a scanning system, which is capable of performing a wide-field retinal scan, is described in WO 2014/53824 A1, the content of which is hereby incorporated by reference in its entirety. Components of such a scanning system are shown in FIG. 5 and comprise an optical coupler 111, a first scanning element 112, a first curved mirror 113, a second scanning element 114 and a second curved mirror 115. The light beam $L_b$ enters the scanning system 110 via the optical coupler 111. The light beam $L_b$ is then reflected, in sequence, by the first scanning element 112, the first curved mirror 113, the second scanning element 114 and the second curved mirror 115, before being incident on the imaging target 140. The light $L_c$ which has been scattered by the imaging target 140 and collected by the scanning system 110 follows the same optical path through the scanning system 110 as the light beam $L_b$ but in reverse order, and exits the scanning system 110 via the optical coupler 111.

The two-dimensional point scan is performed by the first scanning element 112 rotating around a first axis 116 to scan the light beam $L_b$ in a first direction across the imaging target 140, and by the second scanning element 114 rotating around a second axis 117 to scan the light beam $L_b$ in a second direction across the imaging target 140 (which may, as in the present example embodiment, be orthogonal to the first direction). Thus, by rotating the first scanning element 112 and the second scanning element 114, it is possible to steer the light beam $L_b$ to any position on the imaging target 140. The rotation of the first scanning element 112 and the second scanning element 114 may be coordinated by a scanning system controller (not shown) such that the light beam $L_b$ is scanned across the imaging target 140 in accordance with a predefined scan pattern, as discussed above.

In the example of FIG. 5, the first curved mirror 113 is an ellipsoidal mirror (and referred to as a slit mirror), and the second curved mirror 115 is also an ellipsoidal mirror. Each of the ellipsoidal mirrors has two focal points. The first scanning element 112 is disposed at a first focal point of the first curved mirror 113, and the second scanning element 114 is disposed at a second focal point of the first curved mirror 113. The second scanning element 114 is also disposed at a first focal point of the second curved mirror 115, and the imaging target 140 (more specifically, the pupil of the eye in the present example) is disposed at a second focal point of the second curved mirror 115.

The first scanning element 112 and the second scanning element 114 may, as in the present example embodiment, each be a galvanometer optical scanner (or "galvo"), although another type of scanning element could alternatively be used, such as a MEMS scanning mirror or a resonant scanning mirror, for example.

Referring again to FIG. 4, the light detector 120 may, as in the present example embodiment, be a balanced detector comprising a first photodetector 124-1 and a second photodetector 124-2, each photodetector being provided in the form of a photodiode in this example (although other forms of photodetector could alternatively be used). The light detector 120 also has a transimpedance amplifier 128, which generates a voltage detection signal $S_d$ based on a difference between the output photocurrents of the first photodetector 124-1 and second photodetector 124-2. The first photodetector 124-1 and the second photodetector 124-2 are arranged to detect interference light $L_{i1}$ and $L_{i2}$, respectively, which result from an interference between the reference light $L_r$ and the light $L_c$ collected by the scanning system 110 during the point scan, which are superimposed at the beam splitter 310. The first photodetector 124-1 receives interference light $L_{i1}$ via a first light detection aperture 122-1, which is provided in the form of an end of a core of a third optical fibre 125-1, and the second photodetector 124-2 receives interference light $L_{i2}$ via a second light detection aperture 122-2, which is provided in the form of an end of a core of a fourth optical fibre 125-2. The third optical fibre 125-1 and the fourth optical fibre 125-2 may, as in the present example embodiment, both be multi-mode optical fibres and serve to guide light from the detection aperture 122-1 and 122-2, respectively, to the respective photodetectors 124-1 and 124-2. These multi-mode optical fibres may or may not have the same diameter. It should be noted, however, that interference lights $L_{i1}$ and $L_{i2}$ need not be guided to photodetectors 124-1 and 124-2 by optical fibres 125-1 and 125-2, and may be collected by the photodetectors 124-1 and 124-2 directly, via respective detection apertures each provided in the form of a pinhole, window or the like that is formed as part of the photodetector.

Reference light $L_r$ interferes with all of the light $L_c$ collected by the scanning system 110 during the point scan. As the light $L_c$ includes a degree of defocusing, it may have a larger beam size than the light beam $L_b$ generated by the light beam generator 150. Hence, it may also have a larger beam size than the reference light $L_r$, as the reference light aperture 155-1 and light source aperture 155-2 are the same size in the present example embodiment because the same kind of single mode fibre is used for both the first optical fibre 154-1 and the second optical fibre 154-2. To ensure all the collected light $L_c$ interferes with the reference light $L_r$, the first optical system 121 (e.g. one or more lenses) is included in the SS-OCT imaging system 300 to reduce the beam size of collected light $L_c$ such that it is equal to or smaller than the beam size of reference light $L_r$. Alternatively, rather than reducing the beam size of the collected light $L_c$, the reference light beam $L_r$ may be enlarged, either by an optical element (e.g. one or more lenses) through which the reference light $L_r$ passes or by using a larger reference light aperture 155-1, e.g. by using a larger diameter optical fibre as optical fibre 154-1 than optical fibre 154-2.

Although the use of a balanced photodetector is generally preferable for achieving increased signal-to-noise, it may be replaced with a single photodetector in some example embodiments. In such variants, only one of photodetectors 124-1 and 124-2 as described above would be retained, and the transimpedance amplifier 128 would be omitted, with the single photodetector outputting the detection signal $S_d$ to the OCT data processing hardware 130.

In the present example embodiment, multi-mode optical fibres 125-1 and 125-2 are used to provide respective detection apertures 122-1 and 122-2 and guide the interference lights $L_{i1}$ and $L_{i2}$ to the photodetectors 124-1 and 124-2. This is a notable difference from conventional confocal point-scan FD-OCT imaging systems, where single-mode optical fibres normally serve these purposes. This is because the sample arm and reference arm of the interferometer in such conventional systems are typically implemented using single-mode optical fibres (as the use of multi-mode optical fibres would introduce modal dispersion into the light beams therein). The same single-mode optical fibre is normally used to both transmit the sample beam to the imaging target and transmit light scattered from the imaging target back to the optical coupler that divides the light from the OCT light source to travel along the sample and reference arms of the interferometer. Interference between the scattered light and reference light occurs at the optical coupler.

In this conventional optical set-up, an end of a single-mode optical fibre therefore effectively provides both a light source aperture and a detection aperture, which stands in contrast to the asymmetric arrangement in the present example embodiment, where these apertures are provided by ends of different optical fibres. As the optical fibres 125-1 and 125-2 of the light detector 120 serve to guide interference lights $L_{i1}$ and $L_{i2}$ to respective photodetectors 124-1 and 124-2, modal dispersion is not a concern (as it is only the photon counts at the photodetectors that matter) so there is no requirement for optical fibres 125-1 and 125-2 to be single-mode fibres.

Second Example Embodiment

Figure 6:
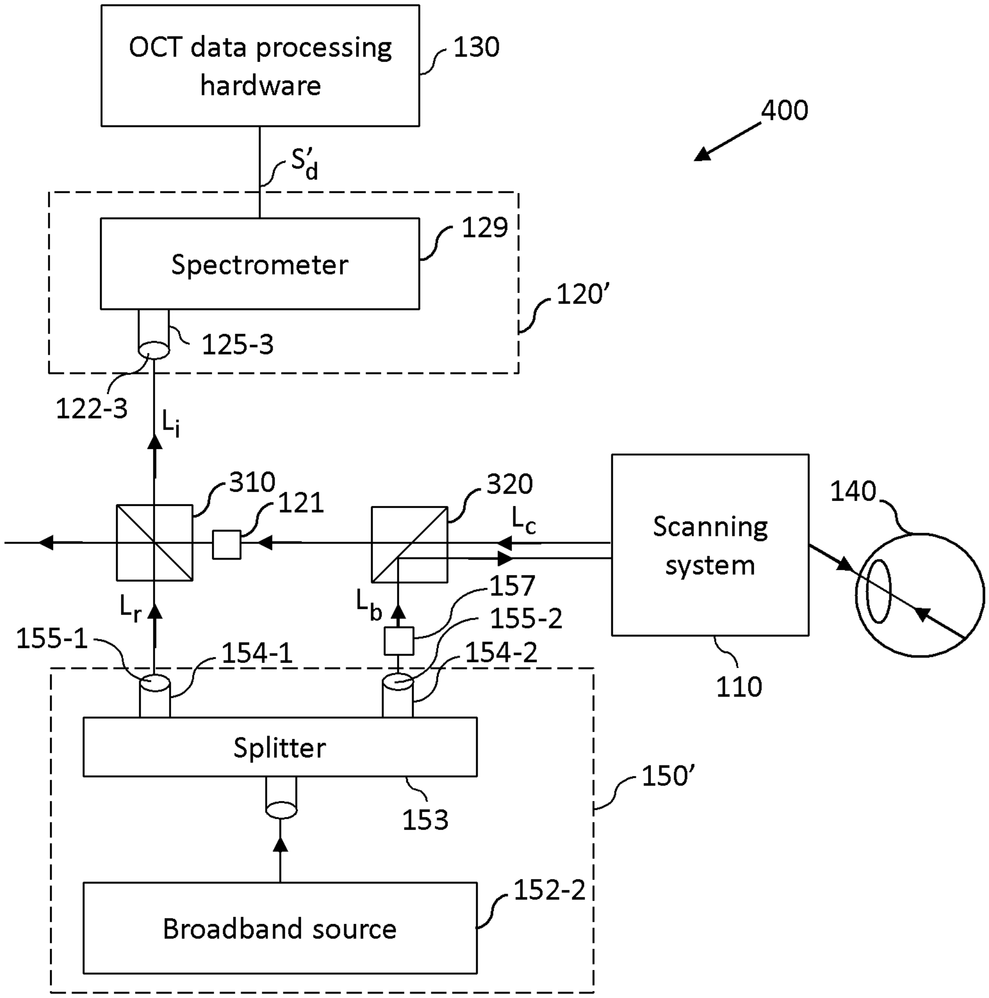
FIG. 6 is a schematic illustration of a non-confocal point-scan spectral-domain OCT imaging system according to a second example embodiment herein.

FIG. 6 is a schematic illustration of a non-confocal point-scan spectral-domain OCT (SD-OCT) imaging system 400 according to a second example embodiment herein.

The SD-OCT imaging system 400 of the present example embodiment comprises a scanning system 110, OCT data processing hardware 130, beam splitters 310 and 320, and a first optical system 121 that are the same as in the first example embodiment. These components, and other components of the SD-OCT imaging system 400 that are labelled with the same reference numerals as in the first example embodiment of FIG. 5, will therefore not be described again. The present embodiment differs from the first example embodiment of FIG. 5 by the configurations of the light detector 120' and the light beam generator 150', and these will now be described with reference to FIG. 6.

The light beam generator 150' comprises a broadband light source 152-2, which may, as in the present example embodiment, be a super-luminescent diode. The light detector 120' comprises a spectrometer 129, which is arranged to measure the spectrum of the interference signal as a function of wavelength of the light. The spectral data may be rescaled and sampled evenly in k-space by the OCT data processing hardware 130, before a Fourier transform is applied to obtain an A-scan.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Some aspects of the examples presented herein, such as the processing of the detection signal $S_d$ to generate complex volumetric OCT data of the imaging target 140, and the correction algorithm 132, may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some or all of the functionality of the OCT data processing hardware 130 may also be implemented by the preparation of application-specific integrated circuits, field-programmable gate arrays, or by interconnecting an appropriate network of conventional component circuits.

A computer program product may be provided in the form of a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The invention claimed is:

1. A point-scan Fourier-domain optical coherence tomography, OCT, imaging system, which is operable to generate complex volumetric OCT data of an imaging target by non-confocal imaging of the imaging target and comprises:
- a splitter arranged to divide light emitted by a light source into a sample beam and a reference beam prior to the sample beam propagating through a first aperture;
- a scanning system arranged to perform a two-dimensional point scan of the sample beam across the imaging target and collect light scattered by the imaging target during the point scan;
- a light detector arranged to generate a detection signal based on an interference light, received through a second aperture different than the first aperture, resulting from an interference between the reference beam and the light collected by the scanning system during the point scan; and
- OCT data processing hardware arranged to:
  - generate the complex volumetric OCT data of the imaging target based on the detection signal, wherein the complex volumetric OCT data, when processed to generate an enface projection of the complex volumetric OCT data, provides an enface projection having at least one of a defocusing or a distortion therein; and
  - generate corrected complex volumetric OCT data by executing a correction algorithm which uses phase information encoded in the complex volumetric OCT data to correct the complex volumetric OCT data, such that the corrected complex volumetric OCT data, when processed to generate an enface projection of the corrected complex volumetric OCT data, provides an enface projection having less of the at least one of the defocusing or the distortion than the enface projection of the complex volumetric OCT data.

2. The point-scan Fourier-domain OCT imaging system according to claim 1, further comprising:
- a light beam generator comprising the light source, the first aperture as a light source aperture, and a first optical system, the light source being arranged to emit light through the first optical system via the light source aperture to generate the sample beam,
- wherein the light detector comprises the second aperture as a detection aperture and a second optical system, the light detector being arranged to detect the interference light propagating through the detection aperture via the second optical system, and
- wherein a size of the detection aperture normalized to a focal length of the second optical system is larger than a size of the light source aperture normalized to a focal length of the first optical system.

3. The point-scan Fourier-domain OCT imaging system according to claim 2, wherein the light source aperture is provided by an end of a core of a first optical fiber and the detection aperture is provided by an end of a core of a second optical fiber.

4. The point-scan Fourier-domain OCT imaging system according to claim 3, wherein the first optical fiber is a single-mode optical fiber.

5. The point-scan Fourier-domain OCT imaging system according to claim 3, wherein the second optical fiber is a multi-mode optical fiber.

6. The point-scan Fourier-domain OCT imaging system according to claim 1, wherein the scanning system comprises a scanning element and a curved mirror, wherein the scanning system is arranged to perform the two-dimensional point scan by the scanning element scanning the sample beam across the imaging target via the curved mirror.

7. The point-scan Fourier-domain OCT imaging system according to claim 6, wherein the curved mirror comprises an ellipsoidal mirror.

8. The point-scan Fourier-domain OCT imaging system according to claim 1, which is at least one of a non-confocal point-scan swept-source OCT imaging system and a non-confocal point-scan spectral-domain OCT imaging system.

9. A computer-implemented method of processing complex volumetric OCT data of an imaging target generated by a point-scan Fourier-domain optical coherence tomography, OCT, imaging system, which is operable to generate the complex volumetric OCT data by non-confocal imaging of the imaging target, the point-scan Fourier-domain OCT imaging system comprising:
- a splitter arranged to divide light emitted by a light source into a sample beam and a reference beam prior to the sample beam propagating through a first aperture;
- a scanning system arranged to perform a two-dimensional point scan of the sample beam across the imaging target and collect light scattered by the imaging target during the point scan;
- a light detector arranged to generate a detection signal based on an interference light, received through a second aperture different than the first aperture, resulting from an interference between the reference beam and the light collected by the scanning system during the point scan; and OCT data processing hardware arranged to generate the complex volumetric OCT data based on the detection signal, wherein the complex volumetric OCT data, when processed to generate an enface projection of the complex volumetric OCT data, provides an enface projection having at least one of a defocusing or a distortion therein, the method comprising:

acquiring the complex volumetric OCT data of the imaging target from the OCT data processing hardware; and generating corrected complex volumetric OCT data by executing a correction algorithm which uses phase information encoded in the complex volumetric OCT data to correct the complex volumetric OCT data, such that the corrected complex volumetric OCT data, when processed to generate an enface projection of the corrected complex volumetric OCT data, provides an enface projection having less of the at least one of the defocusing or the distortion than the enface projection of the complex volumetric OCT data.

10. The computer-implemented method according to claim 9, wherein the point-scan Fourier-domain OCT imaging system further comprises:

a light beam generator comprising the light source, the first aperture as a light source aperture, and a first optical system, the light source being arranged to emit light through the first optical system via the light source aperture to generate the sample beam, wherein the light detector comprises the second aperture as a detection aperture and a second optical system, the light detector being arranged to detect the interference light propagating through the detection aperture via the second optical system, and wherein a size of the detection aperture normalized to a focal length of the second optical system is larger than a size of the light source aperture normalized to a focal length of the first optical system.

11. The computer-implemented method according to claim 10, wherein the light source aperture is provided by an end of a core of a first optical fiber and the detection aperture is provided by an end of a core of a second optical fiber.

12. The computer-implemented method according to claim 11, wherein the first optical fiber is a single-mode optical fiber.

13. The computer-implemented method according to claim 11, wherein the second optical fiber is a multi-mode optical fiber.

14. The computer-implemented method according to claim 9, wherein the scanning system comprises a scanning element and a curved mirror, wherein the scanning system is arranged to perform the two-dimensional point scan by the scanning element scanning the sample beam across the imaging target via the curved mirror.

15. A non-transitory storage medium storing computer-readable instructions which, when executed by a processor, cause the processor to perform a method of processing complex volumetric OCT data of an imaging target generated by a point-scan Fourier-domain optical coherence tomography, OCT, imaging system operable to generate the complex volumetric OCT data by non-confocal imaging of the imaging target, the point-scan Fourier-domain OCT imaging system comprising:

a splitter arranged to divide light emitted by a light source into a sample beam and a reference beam prior to the sample beam propagating through a first aperture;

a scanning system arranged to perform a two-dimensional point scan of the sample beam across the imaging target and collect light scattered by the imaging target during the point scan;

a light detector arranged to generate a detection signal based on an interference light, received through a second aperture different from the first aperture, resulting from an interference between the reference beam and the light collected by the scanning system during the point scan; and OCT data processing hardware arranged to generate the complex volumetric OCT data based on the detection signal, wherein the complex volumetric OCT data, when processed to generate an enface projection of the complex volumetric OCT data, provides an enface projection having at least one of a defocusing or a distortion therein, the method comprising:

acquiring the complex volumetric OCT data of the imaging target from the OCT data processing hardware; and generating corrected complex volumetric OCT data by executing a correction algorithm which uses phase information encoded in the complex volumetric OCT data to correct the complex volumetric OCT data, such that the corrected complex volumetric OCT data, when processed to generate an enface projection of the corrected complex volumetric OCT data, provides an enface projection having less of the at least one of the defocusing or the distortion than the enface projection of the complex volumetric OCT data.

16. The non-transitory storage medium according to claim 15, wherein the point-scan Fourier-domain OCT imaging system further comprises:

a light beam generator comprising the light source, the first aperture as a light source aperture, and a first optical system, the light source being arranged to emit light through the first optical system via the light source aperture to generate the sample beam, wherein the light detector comprises the second aperture as a detection aperture and a second optical system, the light detector being arranged to detect the interference light propagating through the detection aperture via the second optical system, and wherein a size of the detection aperture normalized to a focal length of the second optical system is larger than a size of the light source aperture normalized to a focal length of the first optical system.

17. The non-transitory storage medium according to claim 16, wherein the light source aperture is provided by an end of a core of a first optical fiber and the detection aperture is provided by an end of a core of a second optical fiber.

18. The non-transitory storage medium according to claim 17, wherein:

the first optical fiber is a single-mode optical fiber; and the second optical fiber is a multi-mode optical fiber.

19. The non-transitory storage medium according to claim 15, wherein the scanning system comprises a scanning element and a curved mirror, wherein the scanning system is arranged to perform the two-dimensional point scan by the scanning element scanning the sample beam across the imaging target via the curved mirror.

20. The point-scan Fourier-domain OCT imaging system according to claim 1, wherein:

a size of the second aperture normalized to a focal length of an optical system associated with the second aperture is larger than a size of the first aperture normalized to a focal length of an optical system associated with the first aperture.

* * * * *